US009955936B2

(12) United States Patent
Totsuka et al.

(10) Patent No.: US 9,955,936 B2
(45) Date of Patent: May 1, 2018

(54) X-RAY DIAGNOSTIC APPARATUS

(71) Applicant: Toshiba Medical Systems Corporation, Otawara-shi (JP)

(72) Inventors: Yuki Totsuka, Nasushiobara (JP); Masaharu Soya, Otawara (JP); Ryuji Zaiki, Utsunomiya (JP); Masahiro Ozawa, Sakura (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 109 days.

(21) Appl. No.: 14/678,353

(22) Filed: Apr. 3, 2015

(65) Prior Publication Data
US 2015/0272533 A1 Oct. 1, 2015

Related U.S. Application Data

(63) Continuation of application No. PCT/JP2013/081298, filed on Nov. 20, 2013.

(30) Foreign Application Priority Data

Nov. 26, 2012 (JP) .................................. 2012-257725

(51) Int. Cl.
*G01N 5/00* (2006.01)
*A61B 6/00* (2006.01)
*A61B 6/06* (2006.01)

(52) U.S. Cl.
CPC .............. *A61B 6/541* (2013.01); *A61B 6/06* (2013.01); *A61B 6/463* (2013.01); *A61B 6/467* (2013.01); *A61B 6/487* (2013.01)

(58) Field of Classification Search
CPC ........... A61B 6/06; A61B 6/463; A61B 6/467; A61B 6/487; A61B 6/541; A61B 8/00;
(Continued)

(56) References Cited

U.S. PATENT DOCUMENTS 6,501,828 B1 * 12/2002 Popescu ................... A61B 6/06
378/145
7,113,569 B2 * 9/2006 Okumura ............... A61B 6/032
378/150
(Continued)

FOREIGN PATENT DOCUMENTS

CN 101953691 A 1/2011
JP H09-248294 A 9/1997
(Continued)

OTHER PUBLICATIONS

International Search Report dated Dec. 24, 2013 for PCT/JP2013/081298 filed on Nov. 20, 2013 with English Translation.
(Continued)

*Primary Examiner* — Irakli Kiknadze
(74) *Attorney, Agent, or Firm* — Oblon, McClelland, Maier & Neustadt, L.L.P.

(57) ABSTRACT

According to one embodiment, An X-ray diagnostic apparatus includes an X-ray generator that generates X rays, an X-ray detector that detects the X rays generated by the X-ray generator and having passed through a subject, an X-ray restrictor that restricts an irradiation range on a detection surface of the X-ray detector of the X rays generated by the X-ray generator, a signal input unit that inputs a biomedical signal related to the subject, a signal detector that detects a biomedical change from the biomedical signal and also outputs an extension switching signal, and an X-ray restrictor controller that controls the X-ray restrictor such that the irradiation range of the X rays is extended in response to output of the extension switching signal.

14 Claims, 7 Drawing Sheets

(58) Field of Classification Search
CPC ............ A61B 2560/0431; A61B 5/055; A61B
5/7475; A61B 6/4405; A61B 8/4405;
A61B 8/468; A61B 19/322; G01C
21/3608; G01C 21/3629; G01C 21/3641;
G01C 21/3691; G06F 17/2735; G06F
17/28; G06F 19/322; G06F 19/328; G06F
19/3406; G06F 19/3456; G06F 21/10;
G06F 21/6218; G10L 13/00; G10L 15/08;
G10L 15/26; G10L 17/02; A61N
2005/1074; A61N 5/1038; A61N 5/1049;
A61N 5/1067; A61N 5/1071; A63F
2300/572; G01R 23/16
USPC ................................. 378/62, 4, 19, 147–152
See application file for complete search history.

(56) References Cited

U.S. PATENT DOCUMENTS

| | | | | |
|---|---|---|---|---|
| 7,225,013 | B2* | 5/2007 | Geva | A61B 5/04012 600/481 |
| 7,542,544 | B2* | 6/2009 | Rubin | A61B 6/488 378/62 |
| 2003/0033151 | A1* | 2/2003 | Vozick | A61B 5/7475 704/275 |
| 2003/0068011 | A1* | 4/2003 | Johnson | A61B 5/7475 378/115 |
| 2007/0253526 | A1* | 11/2007 | Bruder | A61B 6/032 378/8 |
| 2011/0013742 | A1 | 1/2011 | Zaiki et al. | |
| 2012/0045034 | A1* | 2/2012 | Hummel | A61B 6/06 378/62 |
| 2012/0057674 | A1* | 3/2012 | Zhang | A61B 5/7285 378/62 |

FOREIGN PATENT DOCUMENTS

| | | |
|---|---|---|
| JP | 2008-212550 A | 9/2008 |
| JP | 2011-118053 A | 6/2011 |
| JP | 2012-075782 A | 4/2012 |
| JP | 2012-228434 A | 11/2012 |

OTHER PUBLICATIONS

Written Opinion dated Dec. 24, 2013 for PCT/JP2013/081298 filed on Nov. 20, 2013.

Combined Chinese Office Action and Search Report dated Aug. 27, 2015 in Patent Application No. 201380003268.4 (with English translation of categories of cited documents).

* cited by examiner

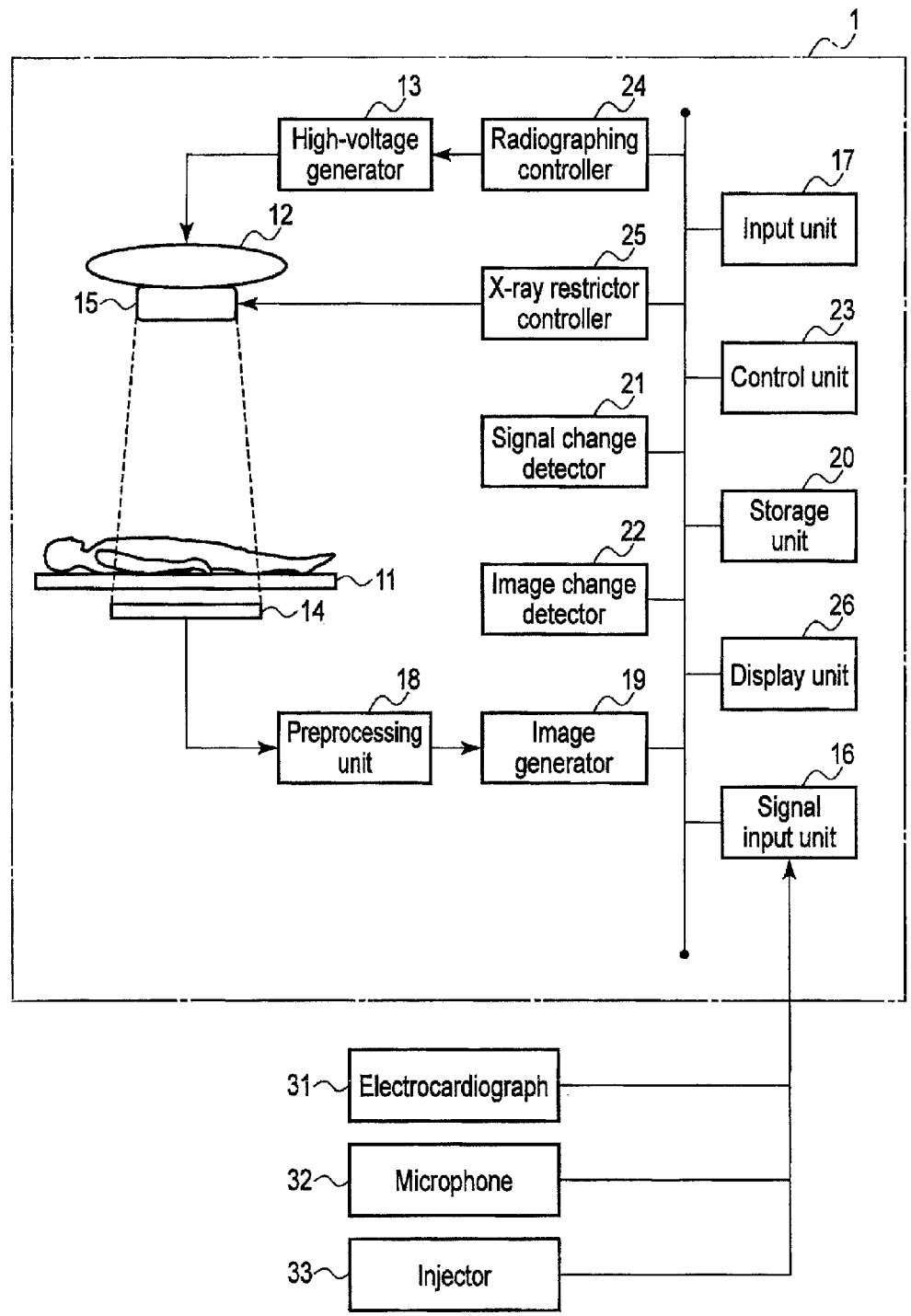
F I G. 1

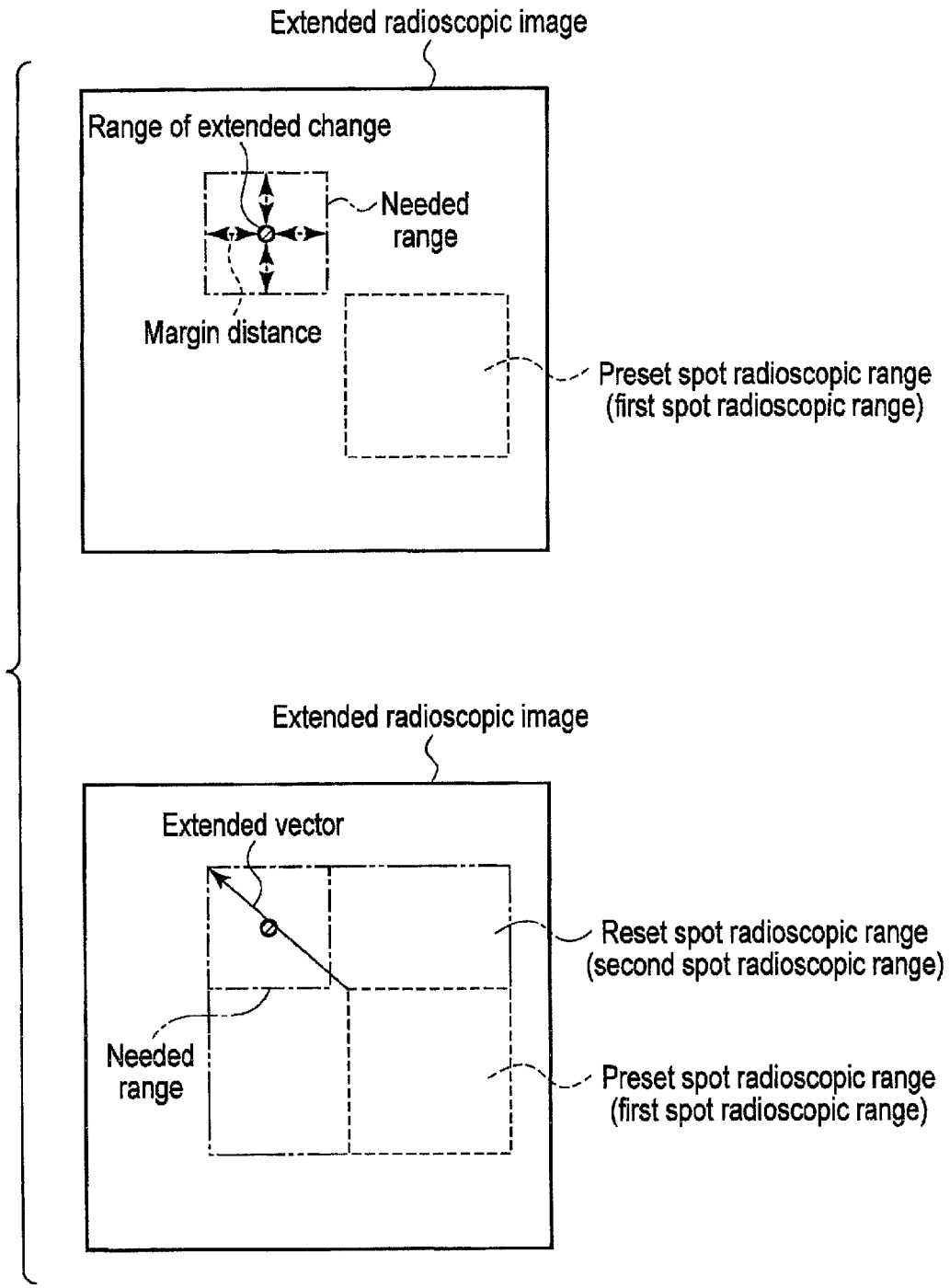
F I G. 6

X-RAY DIAGNOSTIC APPARATUS

CROSS-REFERENCE TO RELATED APPLICATIONS

This application is a Continuation Application of PCT Application No. PCT/JP2013/081298, filed Nov. 20, 2013 and based upon and claims the benefit of priority from the Japanese Patent Application No. 2012-257725, filed Nov. 26, 2012, the entire contents of all of which are incorporated herein by reference.

FIELD

Embodiments described herein relate generally to an X-ray diagnostic apparatus.

BACKGROUND

In recent years, the development of technology to reduce exposed doses in radiography using an X-ray diagnostic apparatus is making progress. As one of such technologies, a spot radioscopic function used for catheter treatment using an X-ray diagnostic apparatus is known. In the spot radioscopic function, the user specifies a region of interest desired to be irradiated with X rays on a radioscopic monitor. Then, an X-ray restrictor is controlled by the X-ray diagnostic apparatus so that the region of interest is irradiated with X rays. Then, a radioscopic image concerning the region of interest by spot radioscopy is superimposed on a full radioscopic still image (last image hold: hereinafter called the LIH image) immediately before the spot radioscopy and displayed. Thus, while the spot radioscopic function provides a radioscopic image that is not much disadvantageous to the maneuver when compared with conventional radioscopy, the X-ray irradiation range is a region of interest and thus, when compared with conventional radioscopy, doses of X-ray exposure can be reduced.

However, the range in which the display is updated in real time is the region of interest specified by the user in advance. In the range outside the region of interest, the LIH image is displayed and thus, a problem is posed that if a change occurs in the range in which the LIH image is displayed, the user does not notice the change. Therefore, a change of a subject's condition under treatment may not be immediately confirmed, leading to worsening of the subject's condition.

BRIEF DESCRIPTION OF THE DRAWINGS

FIG. 1 is a block diagram showing an example of a configuration of an X-ray diagnostic apparatus according to the present embodiment.

FIG. 6 is the first explanatory view illustrating a resetting method of a spot radioscopic range by an X-ray restrictor controller of the X-ray diagnostic apparatus according to the present embodiment.

DETAILED DESCRIPTION

Figure 2:
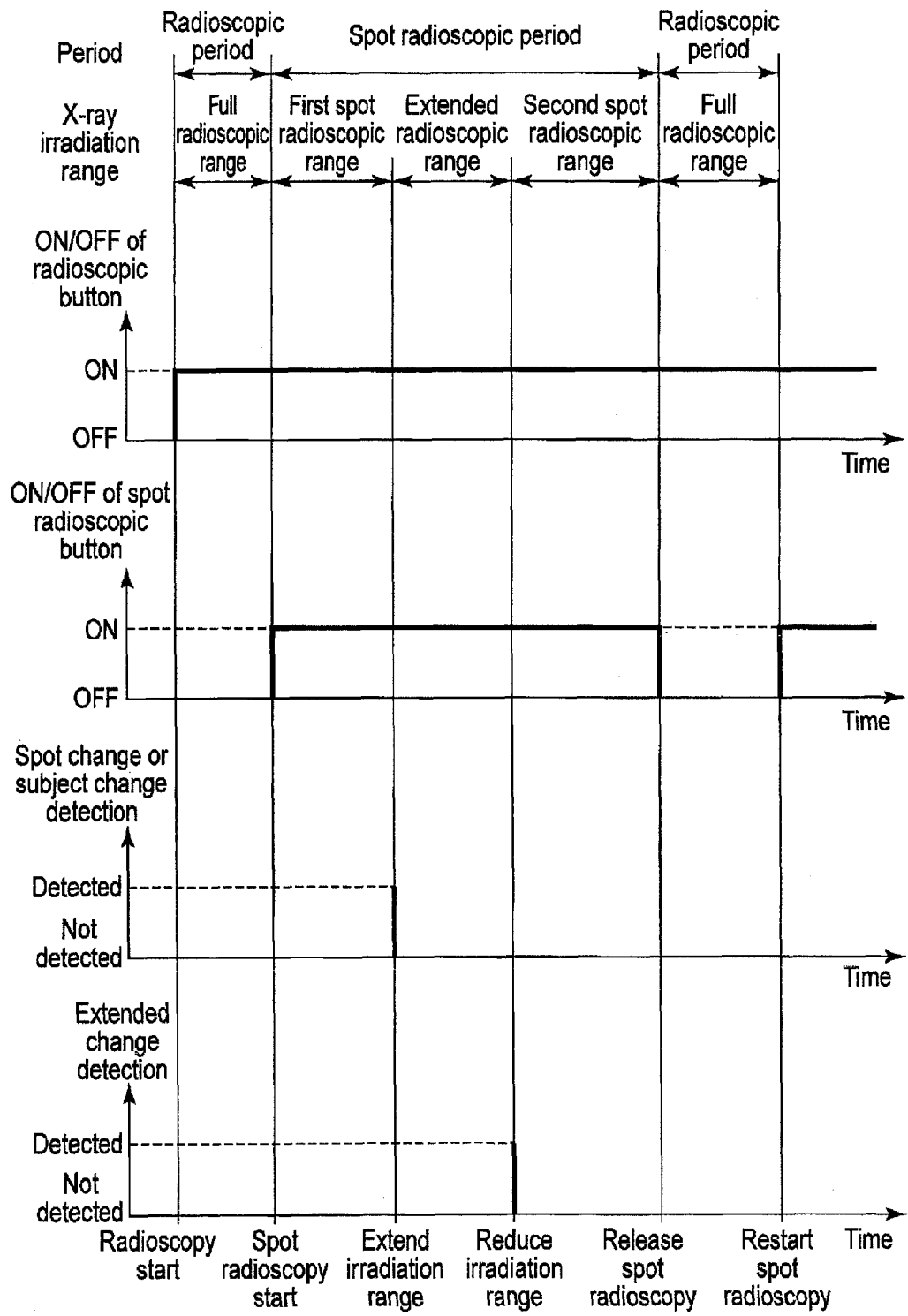
FIG. 2 is an explanatory view illustrating timing of switching an irradiation range of X rays in a sequence of radiographing using the X-ray diagnostic apparatus according to the present embodiment.

An X-ray diagnostic apparatus includes an X-ray generator that generates X rays, an X-ray detector that detects the X rays generated by the X-ray generator and having passed through a subject, an X-ray restrictor that restricts an irradiation range on a detection surface of the X-ray detector of the X rays generated by the X-ray generator, a signal input unit that inputs a biomedical signal related to the subject, a signal detector that detects a biomedical change from the biomedical signal and also outputs an extension switching signal, and an X-ray restrictor controller that controls the X-ray restrictor such that the irradiation range of the X rays is extended in response to output of the extension switching signal.

An X-ray diagnostic apparatus according to the present embodiment will be described below with reference to the drawings. In the description that follows, the same reference signs are attached to elements having substantially the same function and configuration and a duplicate description is provided only when necessary.

FIG. 1 is a block diagram showing an example of the configuration of an X-ray diagnostic apparatus 1 according to the present embodiment. As shown in FIG. 1, the X-ray diagnostic apparatus 1 includes a couch 11, an X-ray generator 12, a high-voltage generator 13, an X-ray detector 14, an X-ray restrictor 15, a signal input unit 16, an input unit 17, a preprocessing unit 18, an image generator 19, a storage unit 20, a signal change detector 21, an image change detector 22, a control unit 23, an radiographing controller 24, an X-ray restrictor controller 25, and a display unit 26.

The couch 11 has a top plate on which a subject is placed. The couch 11 has a moving mechanism to move the top plate in accordance with instructions from the user input via the input unit 17 described later.

The X-ray generator 12 is a vacuum tube that generates X rays. The X-ray generator 12 generates X rays by application of a high voltage (tube voltage) from the high-voltage generator 13. The X-ray generator 12 has a radiation window to radiate generated X rays.

The X-ray detector 14 has a plurality of X-ray detection elements. The plurality of X-ray detection elements is arranged in a two-dimensional array shape. A detector in a two-dimensional array shape is called a flat panel display (FPD). Each element of the FPD is irradiated from the X-ray generator 12 and detects X-rays having passed through a subject. Each element of the FPD outputs an electric signal corresponding to the detected X-ray strength.

The X-ray restrictor 15 (or collimator) is attached between the radiation window of the X-ray generator 12 and a subject, typically attached to the radiation window of the X-ray generator 12. The X-ray restrictor 15 is a cone restricter capable of adjusting the irradiation range of X rays on the detection surface of the X-ray detector 14 and is an apparatus to reduce unnecessary exposure for the subject.

The X-ray restrictor 15 has a plurality of cone restriction blades. One cone restriction blade of the plurality of cone restriction blades is, for example, a blade to set the cone used to the irradiation range of the minimum X rays. The irradiation range of X rays on the detection surface of the X-ray detector 14 is adjusted by each cone restriction blade being operated in accordance with the control of the X-ray restrictor controller 25 described later.

The signal input unit 16 is an external interface to input a biomedical signal, an audio signal, and an operation signal into the X-ray diagnostic apparatus 1. The signal input unit 16 has, for example, a connector portion (not shown) to be connected to an external apparatus via a wire cable or the like to transmit/receive data to/from the external device and a radio signal receiving unit (not shown) to receive a radio signal from the external apparatus.

The biomedical signal is, for example, a blood pressure signal, respiratory signal, brain wave signal, electrocardiographic signal or the like related to a subject. For example, the signal input unit 16 receives input of an electrocardiographic signal from an electrocardiograph 31.

The audio signal is, for example, an audio signal concerning a user treating a subject or conducting surgical operations. The signal input unit 16 receives input of an audio signal from, for example, a microphone 32.

The operation signal is, for example, an operation signal from medical instruments used for treatment, operations and the like of a subject. The operation signal from a medical instrument is, for example, a signal of ON/OFF of an injector 33, a signal about a functional flow reserve (FFR) value or the like. The signal input unit 16 receives input of, for example, an injector signal from the injector 33.

The input unit 17 functions to the X-ray diagnostic apparatus 1 as an interface to receive instruction information by the user. The input unit 17 has an input device such as a mouse, keyboard, trackball, touch panel, button and the like. Particularly the input unit 17 according to the present embodiment has a radioscopic button and a spot radioscopic button. These buttons are frequently operated by physicians during operation and thus are foot buttons. These buttons are buttons to switch the radiographing mode of each unit.

For example, the radiographing mode of each unit is switched from the simple radiographing mode to the first mode (hereinafter, called the full radioscopic mode) with the radioscopic button being trod on. The period in which the radioscopic button is trod on is the radioscopic period.

The radiographing mode of each unit is switched from the radioscopic mode to the second mode (hereinafter, called the spot radioscopic mode) with the spot radioscopic button being trod on. The period in which the spot radioscopic button is trod on together with the radioscopic button is the spot radioscopic period.

The radioscopic button and the spot radioscopic button are not limited to the above foot buttons if structured to be able to switch the radiographing mode as described above. For example, these buttons may be integrated into one foot button so that the radiographing mode is switched based on the amount of being trod on by the user.

The input unit 17 receives input of the irradiation range of X rays in full radioscopic mode (hereinafter, called the full radioscopic range) and the irradiation range of X rays in spot radioscopic mode (hereinafter, called the spot radioscopic range) and also the irradiation range of X rays in extended radioscopic mode described later (hereinafter, called the extended radioscopic range) by the user. The spot radioscopic range is set by the user as a partial range of the full radioscopic range. The extended radioscopic range is set by the user as a range larger than the spot radioscopic range and equal to the full radioscopic range or less. These ranges are defined by, for example, the X-coordinate range and the Y-coordinate range in the two-dimensional XY coordinate system (hereinafter, called the display coordinate system) on the display screen.

The preprocessing unit 18 performs preprocessing on an electric signal output from the X-ray detector 14.

The preprocessing is, for example, various kinds of correction processing, amplification processing, A/D conversion processing or the like.

The image generator 19 generates data of a plurality of radioscopic images based on an electric signal having undergone preprocessing. Data of the plurality of radioscopic images is, for example, data of radioscopic images collected in radioscopic mode (hereinafter, called full radioscopic images), data of a full radioscopic image (last image hold: hereinafter called the LIH image) immediately before the spot radioscopic button is trod on, data of radioscopic images collected in spot radioscopic mode (hereinafter, called spot radioscopic images), data of radioscopic images collected in extended radioscopic mode (hereinafter, called extended radioscopic images) and the like. Therefore, the range of full radioscopic images corresponds to the full radioscopic range. The range of spot radioscopic images corresponds to the spot radioscopic range. The range of extended radioscopic images corresponds to the extended radioscopic range. The pixel value assigned to each pixel constituting an X-ray image is a value corresponding to an X-ray attenuation coefficient of matter on a passing path of X rays or the like.

The storage unit 20 is a semiconductor storage apparatus of a flash SSD (solid state disk) as a semiconductor storage element, HDD (hard disk drive) or the like. The storage unit 20 stores data of a plurality of X-ray images generated by the image generator 19 described above. The storage unit 20 stores a plurality of thresholds for each of signals input into the X-ray diagnostic apparatus 1 via the signal input unit 16. The threshold is, for example, the maximum blood pressure value, the minimum blood pressure value, the fluctuation range of the pulse rate in the unit time and the like. The storage unit 20 stores data of the full radioscopic range, data of the spot radioscopic range, and data of the extended radioscopic range input by the user via the input unit 17.

The signal change detector 21 detects changes (hereinafter, called subject changes together) indicating a condition change of a subject, signs of a condition change of the subject, a change of a radioscopic image and signs of a change of the radioscopic image from biomedical signals, audio signals and operation signals input via the signal input unit 16. The signal change detector 21 detects a subject change and also transmits an extension switching signal to each unit. The extension switching signal is a signal to switch the radiographing mode of each unit from the spot radioscopic mode to the extended radioscopic mode. For example, the X-ray restrictor controller 25 controls the X-ray restrictor 15 in response to reception of the extension switching signal such that the irradiation range of X rays is switched from the spot radioscopic range to the extended radioscopic range. Examples of processing by the signal change detector 21 in accordance with the type of signal input via the signal input unit 16 are described below.

If the input biomedical signal is, for example, a blood pressure signal, the signal change detector 21 acquires the blood pressure values of the subject from the blood pressure signal. The signal change detector 21 determines whether the acquired blood pressure values fall within the normal blood pressure range stored in the storage unit 20. The normal blood pressure range is defined by the threshold of the maximum blood pressure value and the threshold of the minimum blood pressure value stored in the storage unit 20. The signal change detector transmits an extension switching signal to the X-ray restrictor controller 25 in response to the acquired blood pressure value of the subject exceeding the normal blood pressure range.

If the input signal is, for example, an audio signal, the signal change detector 21 analyzes whether the input audio signal contains any signal indicating a specific word. The specific word is, for example, "HIROGETE" (extend in Japanese) or the like. The signal change detector 21 specifies the sound volume from the input audio signal. The signal change detector 21 compares the specified sound volume with the upper limit threshold of sound volume stored in the storage unit 20. The signal change detector 21 transmits an extension switching signal to the X-ray restrictor controller 25 in response to the detection of a specific word from the audio signal and the sound volume exceeding the upper limit threshold.

If the input operation signal is, for example, an injector signal to inject a contrast medium into a subject, the signal change detector 21 detects output of a signal for the notification of the start of injecting a contrast medium from the injector 33. The signal change detector 21 transmits an extension switching signal to the X-ray restrictor controller 25 in response to the detection of a signal for the notification of the start of injecting a contrast medium.

The image change detector 22 detects the range in which an image changes from a full radioscopic image, spot radioscopic image, or extended radioscopic image displayed on the display screen by the display unit 26 described later. The method of detecting an image change includes threshold processing of the average pixel value and differential threshold processing of two images that are temporally arranged one after another.

In the threshold processing of the average pixel value, a matrix to calculate an average pixel value is set by the user in advance. The image change detector 22 specifies a temporal change of the average pixel value of the matrix of, for example, 3 pixels×3 pixels. Then, the image change detector 22 detects a range in which the change value of the average pixel value exceeds a preset threshold as a range in which an image change occurred. Note that the image change detector 22 may detect a range in which the average pixel value exceeds a preset threshold as a range in which an image change occurred. For example, a contrast medium contrast-imaged from an injector becomes dark in an image. Thus, the image change detector 22 can specify a range in which the gray level of the average pixel value exceeds a preset gray level as a range in which contrast imaging is started (the image changes).

In the differential threshold processing of two images that are temporally arranged one after another, a threshold for defining an image change is preset by the user. The image change detector 22 does subtraction of pixel values of corresponding coordinate positions between the two images. Then, the image change detector 22 can specify a range in which the pixel value as a result of the subtraction exceeds a preset threshold as a range in which an image change occurred.

An image change of a full radioscopic image is called a full change. An image change of a spot radioscopic image is called a spot change. An image change of an extended radioscopic image is called an extended change. An image change is, for example, a change before and after removal of thrombus. The image change detector 22 detects an image change based on each pixel value constituting a radioscopic image. The range of a full change, spot change, or extended change is represented by the above display coordinate system.

The image change detector 22 transmits a spot switching signal to each unit together with information in regard to the range of the full change in response to the detection of a full change. The spot switching signal is a signal to switch the radiographing mode of each unit from the full radioscopic mode to the spot radioscopic mode. For example, the X-ray restrictor controller 25 controls the X-ray restrictor 15 such that the irradiation range of X rays is switched from the full radioscopic range to the spot radioscopic range in response to the reception of a spot switching signal.

The image change detector 22 transmits an extension switching signal to each unit in response to the detection of a spot change. The image change detector 22 transmits a spot switching signal to each unit together with information in regard to the range of an extended change in response to the detection of the extended change.

The control unit 23 includes a CPU (Central Processing Unit) and a memory circuit or the like. The control unit receives information input from the input unit 17 and temporally stores the input information in the memory circuit. The control unit 23 controls each unit of the X-ray diagnostic apparatus 1 based on the input information. More specifically, the control unit 23 transmits a full switching signal to each unit in response to the radioscopic button being trod on by the user. The control unit 23 transmits a spot switching signal to each unit in response to the spot radioscopic button being trod on by the user together with the radioscopic button.

The radiographing controller 24 sets radiographing conditions based on information input by the operator via the input unit 17. Radiographing conditions are, for example, the tube voltage, tube current, irradiation time and the like. The tube current in full radioscopic mode, slot radioscopic mode, or extended radioscopic mode is lower than that in simple radiographing mode. The radiographing controller 24 controls each unit concerning the collection of x-ray images. For example, the radiographing controller 24 controls the high-voltage generator 13 based on set radiographing conditions.

The X-ray restrictor controller 25 controls the X-ray restrictor 15 in response to the reception of a full switching signal, spot switching signal, or extension switching signal. The control of the X-ray restrictor 15 by the X-ray restrictor controller 25 indicates that each of a plurality of cone restriction blades constituting the X-ray restrictor 15 is moved by the control of the X-ray restrictor controller 25. Note that the X-ray restrictor controller 25 may control the X-ray restrictor 15 in accordance with instruction information input by the user via the input unit 17. The X-ray restrictor controller 25 resets the spot radioscopic range in response to the reception of a full switching signal. A detailed description of the control of the X-ray restrictor 15 by the X-ray restrictor controller 25 and a detailed description of the resetting method of the spot radioscopic range will be provided later.

The display unit 26 displays a full radioscopic image generated by the image generator 19 on the display screen. The display unit 26 displays a superimposed image in which a spot radioscopic image is superimposed on an LIH image such that anatomical positions match on the display screen.

Next, the timing of switching the irradiation range of X rays in a sequence of radiographing using the X-ray diagnostic apparatus will be described with reference to FIG. 2 according to the present embodiment.

FIG. 2 is an explanatory view illustrating timing of switching the irradiation range of X rays in a sequence of radiographing using the X-ray diagnostic apparatus 1 according to the present embodiment.

As shown in FIG. 2, a full switching signal is transmitted to each unit by the control unit 23 in response to the radioscopic button being trod on. Then, the radiographing mode of each unit is switched from the simple radiographing mode to the full radioscopic mode (first mode). The X-ray restrictor controller 25 controls the X-ray restrictor 15 such that the full radioscopic range (first range) is irradiated with X rays. The full radioscopic range is a fixed range preset by the user via the input unit 17.

A spot switching signal is transmitted to each unit by the control unit 23 in response to the spot radioscopic button being trod on together with the radioscopic button. Then, the radiographing mode of each unit is switched from the full radiographing mode to the spot radioscopic mode (second mode). The X-ray restrictor controller 25 controls the X-ray restrictor 15 such that the irradiation range of X rays is switched from the full radioscopic range to the first spot radioscopic range (second range). The first spot radioscopic range is a range preset by the user via the input unit 17.

An extension switching signal is transmitted to each unit by the control unit 23 in response to the reception of extension switching signals from the signal change detector 21 and the image change detector 22 in a spot radioscopic period. Then, the radiographing mode of each unit is switched from the spot radiographing mode to the extended radioscopic mode (third mode). The X-ray restrictor controller 25 controls the X-ray restrictor 15 such that the irradiation range of X rays is switched from the first spot radioscopic range to the extended radioscopic range (third range). The extended radioscopic range is a fixed range preset by the user via the input unit 17.

A spot switching signal is transmitted to each unit together with information in regard to the range of extended change by the control unit 23 in response to the reception of a spot switching signal from the image change detector 22. The X-ray restrictor controller 25 reset the spot radioscopic range based on the preset spot radioscopic range (first slot radioscopic range) and the range of extended change. The reset spot radioscopic range is called the second spot radioscopic range here. The second spot radioscopic range contains the first spot radioscopic range and the range of extended change. Then, the radiographing mode of each unit is switched from the extended radioscopic range to the spot radioscopic range (fourth mode). The X-ray restrictor controller 25 controls the X-ray restrictor 15 such that the irradiation range of X rays is switched from the extended radioscopic range to the second spot radioscopic range (fourth range).

A radioscopy switching signal is transmitted to each unit by the control unit 23 in response to the spot radioscopic button being released by the user. Then, the spot radioscopic mode of each unit is released. The X-ray restrictor controller 25 controls the X-ray restrictor 15 such that the irradiation range of X rays is switched from the second spot radioscopic range to the full radioscopic range.

In this manner, the X-ray diagnostic apparatus 1 according to the present embodiment can automatically switch the irradiation range of X rays from the spot radioscopic range to the extended radioscopic range in response to the detection of subject change in a spot radioscopic period as a period in which the spot radioscopic button continues to be trod on by the user.

(Automatic Resetting Function)

The automatic resetting function is a function to automatically reset the spot radioscopic range by the X-ray restrictor controller 25 in response to the reception of a spot switching signal from the image change detector 22 in the X-ray diagnostic apparatus 1 according to the present embodiment. The automatic resetting function is applied in the radioscopic period and the spot radioscopic period.

(Automatic Return Function)

The automatic return function is a function to automatically switch the irradiation range of X rays from the spot radioscopic range to the extended radioscopic range by the X-ray restrictor controller 25 in response to the reception of extension switching signals from the signal change detector 21 and the image change detector 22 in a spot radioscopic period of the X-ray diagnostic apparatus 1 according to the present embodiment.

Processing involving the automatic resetting function (hereinafter, called the automatic resetting processing) in a spot radioscopic period will be described with reference to steps S11 to S17 in FIG. 3. Then, processing involving the automatic return function (hereinafter, called the automatic return processing) will be described with reference to steps S18 to S24 in FIG. 3.

Figure 3:
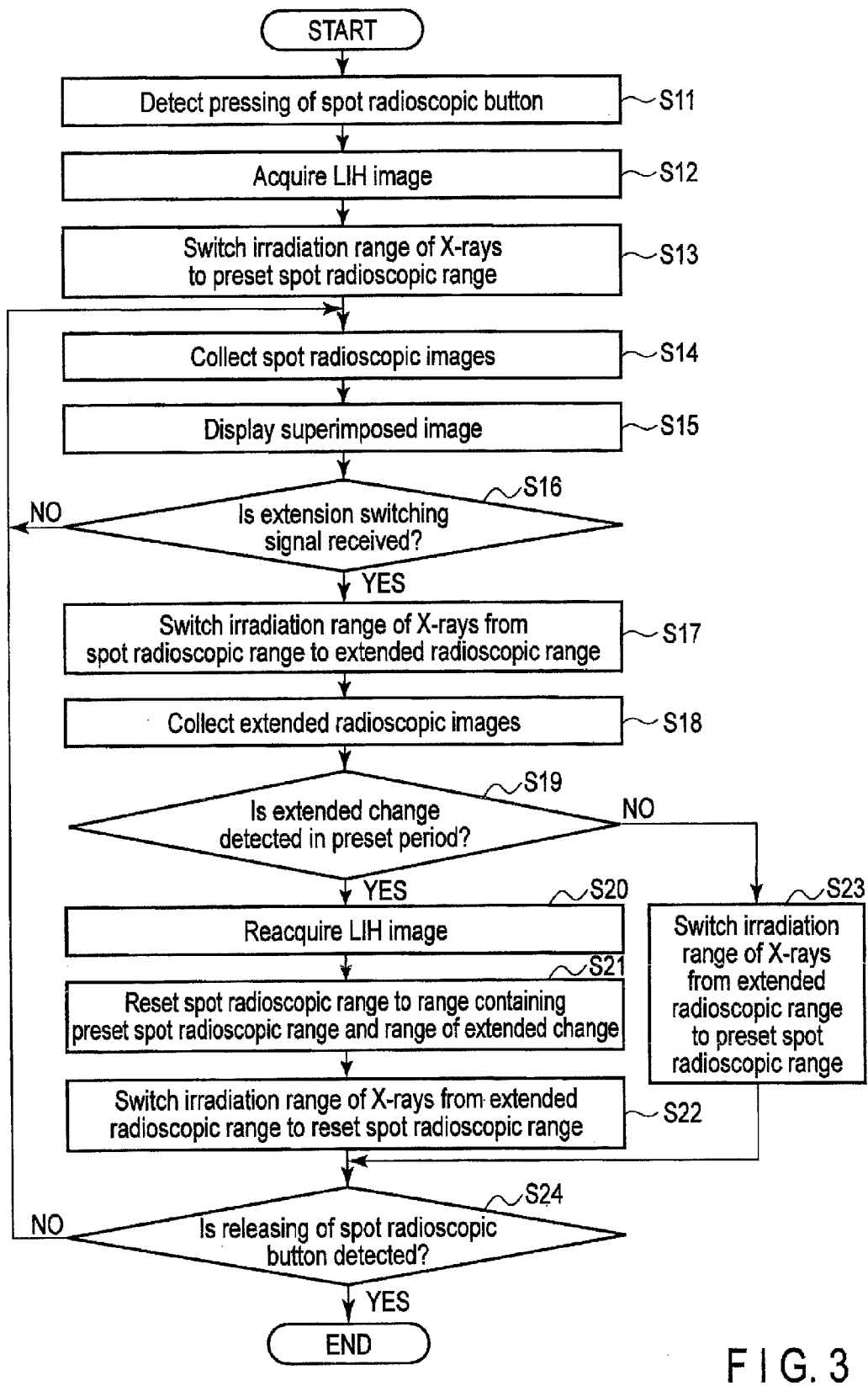
FIG. 3 is a flow chart showing an example of a procedure for automatic return processing and automatic resetting processing in a spot radioscopic period of the X-ray diagnostic apparatus according to the present embodiment.

FIG. 3 is a flow chart showing an example of the procedure for automatic return processing and automatic resetting processing in a spot radioscopic period of the X-ray diagnostic apparatus 1 according to the present embodiment.

(Step S11)

In a radioscopic period, the spot radioscopic button is trod on by the user. A spot switching signal is transmitted to each unit by the control unit 23. The radiographing mode of each unit is switched from the radiographic mode to the spot radiographic mode.

(Step S12)

An LIH image immediately before the spot radioscopic button is trod on is stored in the storage unit 20 by the control unit 23.

(Step S13)

The X-ray restrictor controller 25 controls the X-ray restrictor 15 such that the irradiation range of X rays is switched from the full radioscopic range to the spot radioscopic range.

(Step S14)

The spot radioscopic range is a range preset by the user. Spot radioscopic images corresponding to the spot radioscopic range are collected by each unit in accordance with the control of the radiographing controller 24.

(Step S15)

A superimposed image in which a spot radioscopic image is superimposed on the LIH image such that anatomical positions match is displayed on the display screen by the display unit 26.

(Step S16)

The collection of spot radioscopic images and the display of superimposed images are continued by the X-ray restrictor controller 25 until extension switching signals are received from the signal change detector 21 and the image change detector 22.

(Step S17)

The X-ray restrictor 15 is controlled by the X-ray restrictor controller 25 such that the irradiation range of X rays is switched from the spot radioscopic range to the extended radioscopic range in response to the reception of extension switching signals from the signal change detector 21 and the image change detector 22

(Step S18)

Extended radioscopic images corresponding to the extended radioscopic range are collected by each unit according to the control of the radiographing controller 24.

(Step S19)

An extended radioscopic image is displayed by the display unit 26 in a preset period. If an extended change is detected by the image change detector 22 in the period, the processing moves to step S20. On the other hand, if no extended change is detected by the image change detector 22 in the period, the processing moves to step S23.

(Step S20)

A spot switching signal is transmitted to each unit together with information in regard to the range of extended change in response to the detection of the extended change by the image change detector 22. Data of an LIH image immediately before detection of a full change is stored in the storage unit 20 by the control unit 23 in response to the reception of a spot switching signal. In step S12, data of the LIH image stored in the storage unit 20 and immediately before the spot radioscopic button being trod on may be overwritten with data of the LIH image immediately before detection of a full change, in accordance with user's instructions.

(Step S21)

The spot radioscopic range is reset to a range containing the preset spot radioscopic range and the range of extended change by the X-ray restrictor controller 25.

(Step S22)

The X-ray restrictor 15 is controlled by the X-ray restrictor controller 25 such that the irradiation range of X rays is switched from the extended radioscopic range to the reset spot radioscopic range.

(Step S23)

If no extended change is detected by the image change detector 22 for a preset period, the X-ray restrictor 15 is controlled by the X-ray restrictor controller 25 such that the irradiation range of X rays is switched from the extended radioscopic range to the preset spot radioscopic range.

(Step S24)

The processing in steps S14 to S23 is performed by each unit until the spot radioscopic button is released by the user. When the spot radioscopic button is released by the user, a full switching signal is transmitted to each unit by the control unit 23. The radiographing mode of each unit is switched from the spot radioscopic mode to the full radioscopic mode. Note that if the spot radioscopic button is trod on by the user again, the processing in steps S11 to S23 is performed until the spot radioscopic button is released. In this case, the LIH image on which a spot radioscopic image or an extended radioscopic image is superimposed is the latest LIH image. That is, if the spot radioscopic button is trod on again, the LIH image is the LIH image immediately before the button is trod on.

Next, a display transition on a display screen while the automatic return processing or automatic resetting processing is performed in the spot radioscopic period of the X-ray diagnostic apparatus 1 according to the present embodiment will be described with reference to FIG. 4.

Figure 4:
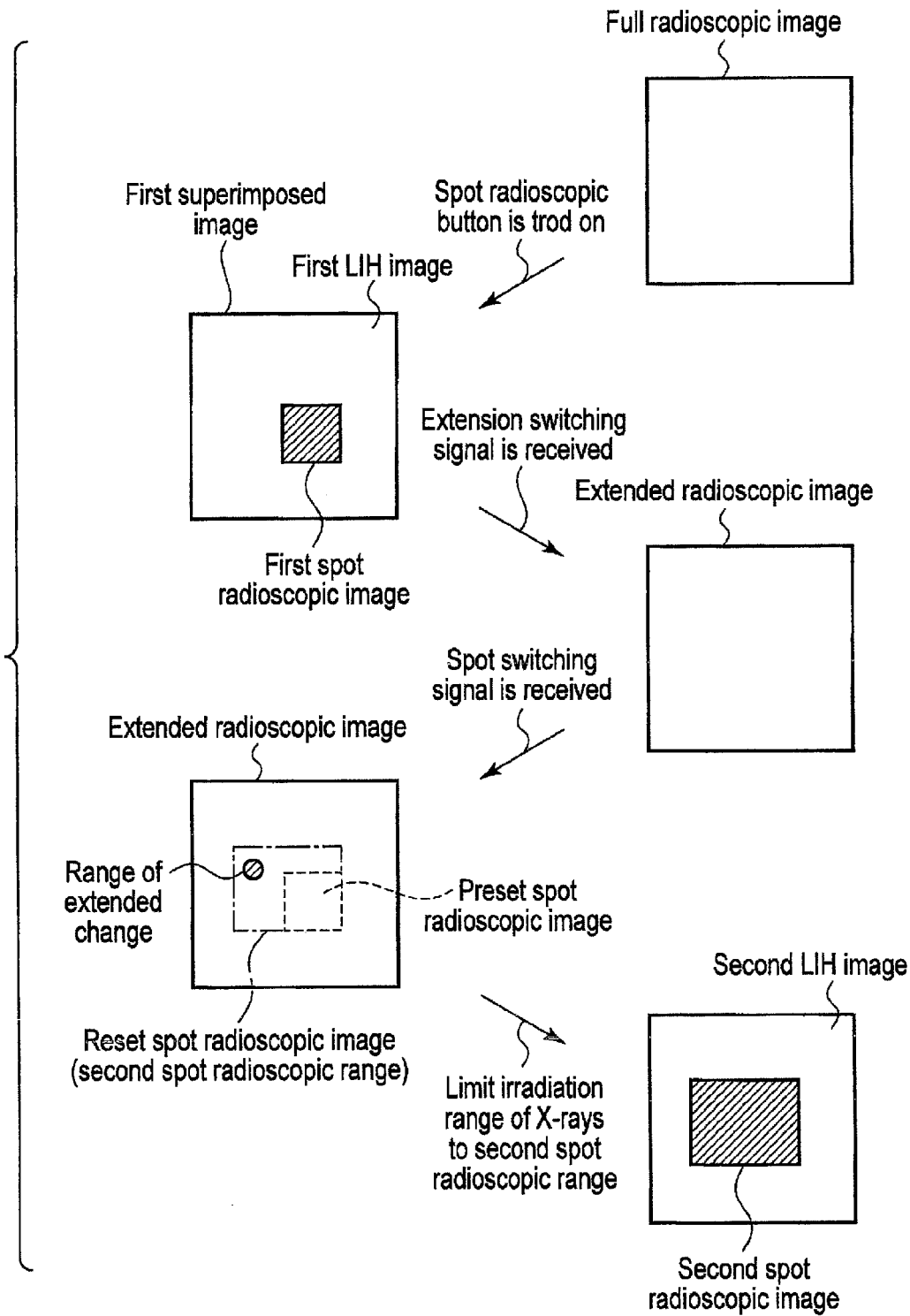
FIG. 4 is an explanatory view illustrating a display transition on a display screen while the automatic return processing or automatic resetting processing is performed in the spot radioscopic period of the X-ray diagnostic apparatus according to the present embodiment.

FIG. 4 is an explanatory view illustrating a display transition on a display screen while the automatic return processing or automatic resetting processing is performed in the spot radioscopic period of the X-ray diagnostic apparatus 1 according to the present embodiment. As shown in FIG. 4, a full radioscopic image is displayed on the display screen by the display unit 26 in response to the radioscopic button being trod on by the user. The first superimposed image is displayed on the display screen by the display unit 26 in response to the spot radioscopic button being trod on by the user together with the radioscopic button. The first superimposed image is an image obtained by the first spot radioscopic image being superimposed on the first LIH image such that anatomical positions match on the display screen. The first spot radioscopic image is a radioscopic image corresponding to the spot radioscopic range preset by the user. The first LIH image is an LIH image collected by each unit immediately before the spot radioscopic button being trod on.

An extended radioscopic image is displayed on the display screen by the display unit 26 in response to the reception of extension switching signals transmitted from the signal change detector 21 and the image change detector 22. The extended radioscopic image is a radioscopic image corresponding to the extended radioscopic range preset by the user.

The second superimposed image is displayed on the display screen by the display unit 26 in response to the reception of a spot switching signal from the image change detector 22. The second superimposed image is an image obtained by the second spot radioscopic image being superimposed on the second LIH image such that anatomical positions match on the display screen. The second spot radioscopic image is a radioscopic image corresponding to the spot radioscopic range (second spot radioscopic range) reset by the X-ray restrictor controller 25. The reset spot radioscopic range contains the preset spot radioscopic range and the range of extended change. The second LIH image is an LIH image collected by each unit immediately before a spot switching signal being received.

Next, the automatic resetting processing in a radioscopic period of the X-ray diagnostic apparatus 1 according to the present embodiment will be described with reference to FIG. 5.

Figure 5:
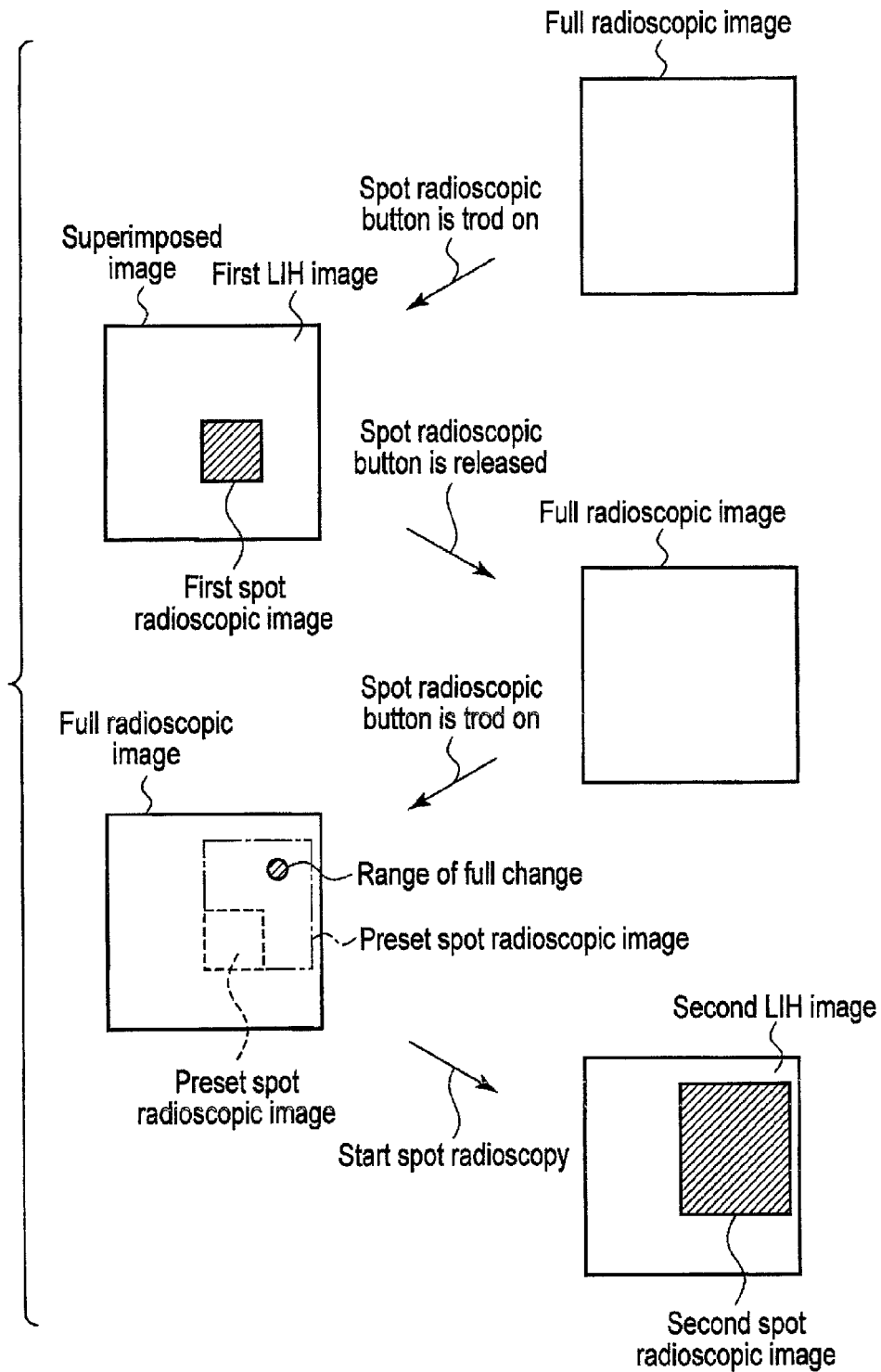
FIG. 5 is an explanatory view illustrating the automatic resetting processing in a radioscopic period of the X-ray diagnostic apparatus according to the present embodiment.

FIG. 5 is an explanatory view illustrating the automatic resetting processing in a radioscopic period of the X-ray diagnostic apparatus 1 according to the present embodiment. As shown in FIG. 5, a full radioscopic image is displayed on the display screen by the display unit 26 in response to the radioscopic button being trod on by the user. The first superimposed image is displayed on the display screen by the display unit 26 with the spot radioscopic button being trod on by the user together with the radioscopic button. The first superimposed image is an image obtained by the first spot radioscopic image being superimposed on the first LIH image such that anatomical positions match on the display screen. The first spot radioscopic image is a radioscopic image corresponding to the spot radioscopic range preset by the user. The first LIH image is an LIH image collected by each unit immediately before the spot radioscopic button being trod on. First LIH images collected are stored in the storage unit 20 by the control unit 23.

A full radioscopic image is displayed by the display unit 26 in response to the slot radioscopic button being released from depressing by the user. The LIH image (hereinafter, called the second LIH image) immediately before the spot radioscopic button being trod on again is collected with the spot radioscopic button being trod on again by the user together with the radioscopic button. Whether there is any full change of the second LIH image with respect to the first LIH image stored in the storage unit 20 is determined by the image change detector 22. If a full change is detected, the spot radioscopic range is reset by the X-ray restrictor controller 25. The reset spot radioscopic range contains the preset spot radioscopic range and the range of extended change. The X-ray restrictor 15 is controlled by the X-ray restrictor controller 25 such that the irradiation range of X rays is switched from the full radioscopic range to the reset spot radioscopic range. Then, the second superimposed image is displayed on the display screen by the display unit 26. The second superimposed image is an image obtained by the second spot radioscopic image being superimposed on the second LIH image such that anatomical positions match on the display screen. The second spot radioscopic image is a radioscopic image corresponding to the reset spot radioscopic range. Second LIH images collected are stored in the storage unit 20 by the control unit 23.

Next, a resetting method of the spot radioscopic range by the X-ray restrictor controller 25 in the automatic resetting processing will be described with reference to FIGS. 6 and 7.

FIG. 6 is the first explanatory view illustrating a resetting method of the spot radioscopic range by the X-ray restrictor controller 25 of the X-ray diagnostic apparatus 1 according to the present embodiment.

Figure 7:
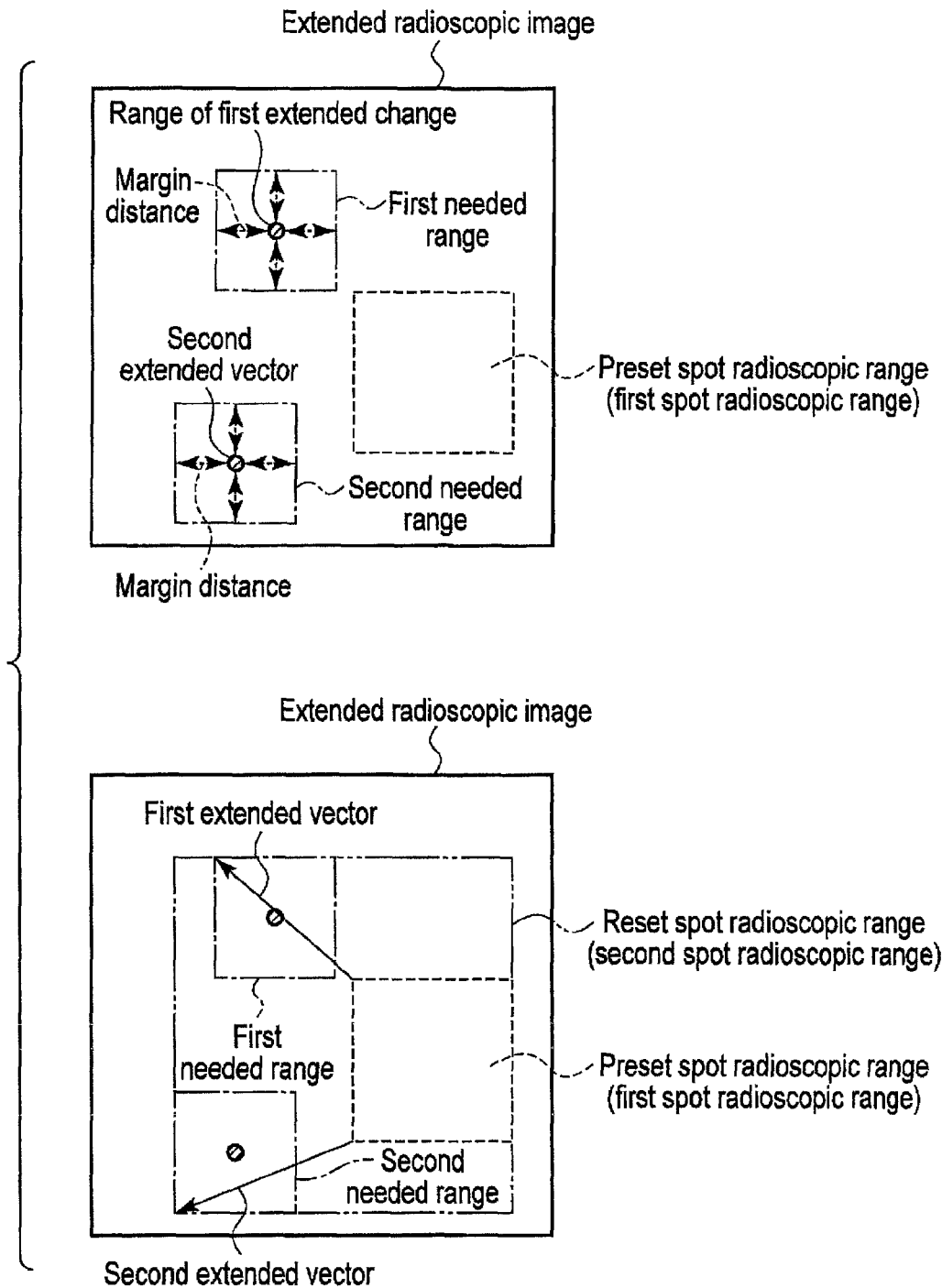
FIG. 7 is the second explanatory view illustrating the resetting method of the spot radioscopic range by the X-ray restrictor controller of the X-ray diagnostic apparatus according to the present embodiment.

FIG. 7 is the second explanatory view illustrating the resetting method of the spot radioscopic range by the X-ray restrictor controller 25 of the X-ray diagnostic apparatus 1 according to the present embodiment.

First, as shown in FIG. 6, a case in which an extended change is detected by the image change detector 22 in one location on an extended image will be described. The range of the extended change is detected by the X-ray restrictor controller 25 and the required range is determined. The required range is a range defined by the range of an extended change and a margin distance around the range of an extended change. An extended vector is determined based on the physical relationship between the preset slot radioscopic range and the required range. The extended vector shows an extension direction and an extended distance. The slot radioscopic range is reset by the X-ray restrictor controller 25 based on the extended vector.

In the event that an extended change is detected by the image change detector 22 in two locations on the extended image as shown in FIG. 7, the above resetting method can also be applied. That is, the range of the first extended change and the range of the second extended change are detected by the X-ray restrictor controller 25 and the first required range and the second required range are determined from the respective ranges. The first extended range is determined based on the preset slot radioscopic range and the first required range. Also, the second extended range is determined based on the preset slot radioscopic range and the second required range. The slot radioscopic range is reset by the X-ray restrictor controller 25 based on the first extended vector and the second extended vector.

According to the automatic resetting function described above, the following effects can be obtained:

According to the X-ray diagnostic apparatus 1 in the present embodiment including the automatic resetting function, an extended change can be detected from an extended radioscopic image in a spot radioscopic period. A spot radioscopic range can automatically be reset in response to the detection of the extended change. Then, the X-ray restrictor controller 25 controls the X-ray restrictor 15 such that the reset spot radioscopic range is irradiated with X rays. In the reset spot radioscopic range, the spot radioscopic range preset by the user and the range of the extended change are included. The extended change may be related to a condition change of a subject. Thus, the user can diagnose and treat the subject while checking for any condition change of the subject by browsing the spot radioscopic image corresponding to the reset spot radioscopic range. Therefore, the X-ray diagnostic apparatus 1 according to the present embodiment can reduce the probability of the user overlooking a worsening condition of the subject in treatment using radiographing or the like.

According to the X-ray diagnostic apparatus 1 in the present embodiment including the automatic resetting function, each time a spot radioscopic button is trod on by the user in a radioscopic period, whether there is any full change from the LIH image collected in the past is determined. Accordingly, the spot radioscopic range can automatically be reset in response to the detection of a full change. Then, the X-ray restrictor controller 25 controls the X-ray restrictor 15 such that the reset spot radioscopic range is irradiated with X rays.

The reset spot radioscopic range contains the preset spot radioscopic range and the range of full change. The full change may be related to a condition change of a subject. Thus, the user can diagnose and treat the subject while checking for any condition change of the subject by browsing the spot radioscopic image corresponding to the reset spot radioscopic range. Therefore, the X-ray diagnostic apparatus 1 according to the present embodiment can reduce the probability of the user overlooking a worsening condition of the subject in treatment using radiographing or the like.

According to the automatic return function described above, the following effects can be gained:

According to the X-ray diagnostic apparatus 1 in the present embodiment including the automatic return function, the X-ray restrictor controller 25 controls the X-ray restrictor 15 such that the irradiation range of X rays is switched from the spot radioscopic range to the extended radioscopic range in response to the detection of a subject change. The extended radioscopic range is a range larger than the spot radioscopic range. The subject change may be related to a condition change of a subject. Thus, while browsing a spot radioscopic image corresponding to the spot radioscopic range, in response to the detection of a subject change, the user can browse an extended radioscopic image in which the irradiation range is automatically extended. Then, the user can check causes or the like of the subject change in the extended radioscopic image. Therefore, the X-ray diagnostic apparatus 1 according to the present embodiment can reduce the probability of the user overlooking a worsening condition of the subject in treatment using radiographing or the like.

Note that a plurality of units according to the present embodiment (for instance, the preprocessing unit 18, the image generator 19, the storage unit 20, the signal change detector 21, the image change detector 22, the control unit 23, the radiographing controller 24, the X-ray restrictor controller 25 and the like) may be implemented by processing circuitry. The processing circuitry may be constituted of a singular set of circuitry such as a CPU, plural sets of circuitry corresponding to each of the units, or the combination thereof.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An X-ray diagnostic apparatus comprising:
an X-ray generator that generates X rays;
an X-ray detector that detects the X rays generated by the X-ray generator and having passed through a subject;
an X-ray restrictor that restricts an irradiation range on a detection surface of the X-ray detector of the X rays generated by the X-ray generator;
a signal input unit that inputs a biomedical signal related to the subject;
a signal detector that detects a biomedical change from the biomedical signal and also outputs an extension switching signal according to the biomedical change; and
an X-ray restrictor controller that controls the X-ray restrictor such that the irradiation range of the X rays is extended to a predetermined range in response to output of the extension switching signal.

2. The X-ray diagnostic apparatus according to claim 1, further comprising: an input unit that selects and operates first and second modes having the different irradiation ranges, wherein
the X-ray restrictor controller controls the X-ray restrictor such that a first range of the subject is irradiated with the X rays in a period in which the first mode is maintained, controls the X-ray restrictor such that a second range smaller than the first range of the subject is irradiated with the X rays in the period in which the second mode is maintained, and controls the X-ray restrictor such that a third range larger than the second range of the subject is irradiated with the X rays in response to the output of the extension switching signal in the period in which the second mode is maintained.

3. The X-ray diagnostic apparatus according to claim 2, wherein the third range is a range that matches the first range.

4. The X-ray diagnostic apparatus according to claim 2, wherein the third range is a range larger than the second range and smaller than the first range.

5. The X-ray diagnostic apparatus according to claim 2, further comprising:
an image change detector that detects a partial range of an image change from each of X-ray images corresponding to the third range and also outputs a reduction switching signal, wherein
the X-ray restrictor controller controls the X-ray restrictor such that a fourth range smaller than the third range is irradiated with the X rays in response to the output of the reduction switching signal in the period in which the third range is irradiated with the X rays.

6. The X-ray diagnostic apparatus according to claim 5, wherein the fourth range contains the range of the image change of the X-ray images corresponding to the third range.

7. The X-ray diagnostic apparatus according to claim 5, wherein
the fourth range contains the range of the image change of the X-ray images corresponding to the first range and the third range.

8. An X-ray diagnostic apparatus comprising:
an X-ray generator that generates X rays;
an X-ray detector that detects the X rays generated by the X-ray generator and having passed through a subject;
an X-ray restrictor that restricts an irradiation range on a detection surface of the X-ray detector of the X rays generated by the X-ray generator;
an image generator that generates a plurality of X-ray images related to the subject;
an image change detector that detects a partial range of an image change from each of the X-ray images and also outputs an extension switching signal according to the partial range of the image change; and
an X-ray restrictor controller that controls the X-ray restrictor such that the irradiation range of the X rays is extended to a predetermined range in response to output of the extension switching signal.

9. The X-ray diagnostic apparatus according to claim 8, further comprising: an input unit that selects and operates first and second modes having the different irradiation ranges, wherein
the X-ray restrictor controller controls the X-ray restrictor such that a first range of the subject is irradiated with the X rays in a period in which the first mode is maintained, controls the X-ray restrictor such that a second range smaller than the first range of the subject is irradiated with the X rays in the period in which the second mode is maintained, and controls the X-ray restrictor such that a third range larger than the second range of the subject is irradiated with the X rays in response to the output of the extension switching signal in the period in which the second mode is maintained.

10. The X-ray diagnostic apparatus according to claim 9, wherein the third range is a range that matches the first range.

11. The X-ray diagnostic apparatus according to claim 9, wherein the third range is a range larger than the second range and smaller than the first range.

12. The X-ray diagnostic apparatus according to claim 9, wherein
the image change detector detects the partial range of the image change from each of the X-ray images corresponding to the third range and also outputs a reduction switching signal and
the X-ray restrictor controller controls the X-ray restrictor such that a fourth range smaller than the third range is irradiated with the X rays in response to the output of the reduction switching signal in the period in which the third range is irradiated with the X rays.

13. An X-ray diagnostic apparatus comprising:
an X-ray generator that generates X rays;
an X-ray detector that detects the X rays generated by the X-ray generator and having passed through a subject;
an X-ray restrictor that restricts an irradiation range on a detection surface of the X-ray detector of the X rays generated by the X-ray generator;
a signal input unit that inputs an operation signal from a medical instrument used to treat or operate on the subject;
a signal detector that detects use of the medical instrument from the operation signal and also outputs an extension switching signal according to the detected use; and
an X-ray restrictor controller that controls the X-ray restrictor such that the irradiation range of the X rays is extended to a predetermined range in response to output of the extension switching signal.

14. An X-ray diagnostic apparatus comprising:
an X-ray generator that generates X rays;
an X-ray detector that detects the X rays generated by the X-ray generator and having passed through a subject;

an X-ray restrictor that restricts an irradiation range on a detection surface of the X-ray detector of the X rays generated by the X-ray generator;

a signal input unit that inputs an audio signal of a user involved in treatment or an operation of the subject;

a signal detector that detects at least one of a specific word and a specific sound volume from the audio signal and also outputs an extension switching signal according to the at least one of the specific word and the specific sound volume; and an X-ray restrictor controller that controls the X-ray restrictor such that the irradiation range of the X rays is extended to a predetermined range in response to output of the extension switching signal.

* * * * *